United States Patent [19]

Dürr

[11] 4,049,981

[45] Sept. 20, 1977

[54] PIEZOELECTRICALLY DRIVEN ULTRASONIC TOOL WITH COOLING

[75] Inventor: Walter Dürr, Bissingen, Germany

[73] Assignee: Dürr-Dental KG, Germany

[21] Appl. No.: 640,778

[22] Filed: Dec. 15, 1975

Related U.S. Application Data

[63] Continuation of Ser. No. 450,108, March 11, 1974, abandoned, which is a continuation of Ser. No. 288,887, Sept. 13, 1972, abandoned.

[51] Int. Cl.² .......................................... H01L 41/04
[52] U.S. Cl. .................................. 310/317; 310/314
[58] Field of Search ............... 310/8.1, 8.3, 8.7, 26; 32/50, 58, DIG. 4; 128/24 A, 32; 318/116

[56] References Cited

U.S. PATENT DOCUMENTS

| | | | |
|---|---|---|---|
| 2,874,470 | 2/1959 | Richards | 32/DIG. 4 |
| 3,375,820 | 4/1968 | Kuris | 310/26 X |
| 3,645,255 | 2/1972 | Robinson | 128/24 A |
| 3,760,799 | 9/1973 | Crowson | 128/24 A |
| 3,809,977 | 5/1974 | Balamuth et al. | 318/116 |

*Primary Examiner*—Mark O. Budd
*Attorney, Agent, or Firm*—Robert E. Burns; Emmanuel J. Lobato; Bruce L. Adams

[57] ABSTRACT

A hand held device for generating ultrasonic vibrations comprises an elongated tubular casing having therein a piezoelectric vibrator element and a generator that develops an electrical signal having a predetermined ultrasonic frequency that excites the piezoelectric vibrator element into ultrasonic vibration. A work tool protrudes from the casing and is vibrationally coupled to the piezoelectric vibrator element by a vibratory rod and the rod transmits the vibration from the piezoelectric vibrator element to the work tool. A cooling system is disposed within the casing and flows a cooling agent through the device to cool both the piezoelectric vibrator element and the generator and the cooling agent is discharged from the device in atomized form through an opening in the work tool.

17 Claims, 6 Drawing Figures

PIEZOELECTRICALLY DRIVEN ULTRASONIC TOOL WITH COOLING This is a continuation, of application Ser. No. 450,108, filed Mar. 11, 1974, which is a continuation of application Ser. No. 288,887, filed 9-13, 1972 both now abandoned.

DESCRIPTION OF THE INVENTION

The invention relates to a device for creating ultrasonic vibrations, especially for dental, medical or cosmetic use, where a piezoelectric vibrator is located inside an elongated hand tool and is connected vibrationally with a rod extending outward from the tip of the hand tool and conducting the ultrasonic vibrations, and which includes a generator which creates the electrical vibrations which excite the piezoelectric vibrator unit.

Ultrasonically vibrating devices have been used for quite some time, especially in dentistry, and especially for the removal of tartar from teeth. In these devices, nickel bars or ferrites are excited to resonance frequencies, which lie approximately in the neighborhood of 20-30 kHz. These vibrations provide the driving power for tools used to remove tartar from the teeth.

A known type of piezoelectric tooth cleaning device has a piezoelectric vibrator in the form of a cylindrical tube which occupies nearly the entire piece of equipment. An oscillator is exterior to the tool.

The known type of equipment are relatively large and heavy and take up considerable space, the latter factor being especially distressing in view of the notorious lack of available space around a dentist chair. The generator or vibrator, with its supporting machinery and controls to be operated by the dentist, especially those used for tuning and adjusting the volume, have always been housed in a rather bulky container which, due to the lack of space, could not be kept at the chair normally used by the dentist, so that there was considerable pressure to install the tartar removal apparatus at another location where the dentist could have the switch and adjusting knob at his fingertips while working. This meant that the patient would have to change to a different chair during treatment. Thus the changing of chairs has not only meant a lot of detailed extra adjustments for the dentist but is also inconvenient for the patient himself.

One object of the invention is to avoid the drawbacks of the known type of equipment and to create a compact, properly working ultasonic apparatus that can be installed and used in any situation. In accordance with the invention, the generator is spacially separated from the vibrator element in the hand tool and acoustically insulated from it, and the two units are combined into a single structure. A structural unit of this type, when put together from modern electronic power components, can be made very small, resulting in a considerable saving of space of comparison with the known types of equipment. But above all, the shielded supply line to the hand tool has been eliminated, so that it is now possible to include this device with all the other instruments at the dental chair without using a problematic amount of space. As a rule, the amount of dc voltage required for the power unit is already available or can be manufactured by a power unit located at any convenient place, not necessarily inaccessible to the dentist. This eliminates some of the awkwardness that is experienced with a high frequency line running between the power unit and the hand tool. The power can be turned on and off by a switch on the hand tool. Adequate shielding is provided against vibrations.

The piezoelectric vibrator unit can serve as the frequency-determining element of the generator which excites it, thereby further simplifying the apparatus as a whole, permitting the elimination of tuning problems and other difficulties relating to temperature and frequency. Since the vibrator unit and the generator are located in close proximity to each other, the power line problem is also eliminated.

A cooling agent, such as water, which is needed for the dental chair, may be run through an apparatus of this type. This will at the same time conduct away the heat built up at the generator. The appropriate supply lines bearing the cooling agent may also be vibrationally insulated.

As a piezoelectric vibrator, types of quartz are suitable, since these produce mechanical vibrations when subjected to an ac voltage at their electrodes, these vibrations being communicated to a rod and to whatever tools may be attached to it.

Further details and advantageous arrangements of the invention are treated below, in connection with the description of a preferred form of embodiment shown in the drawings.

Figure 1:
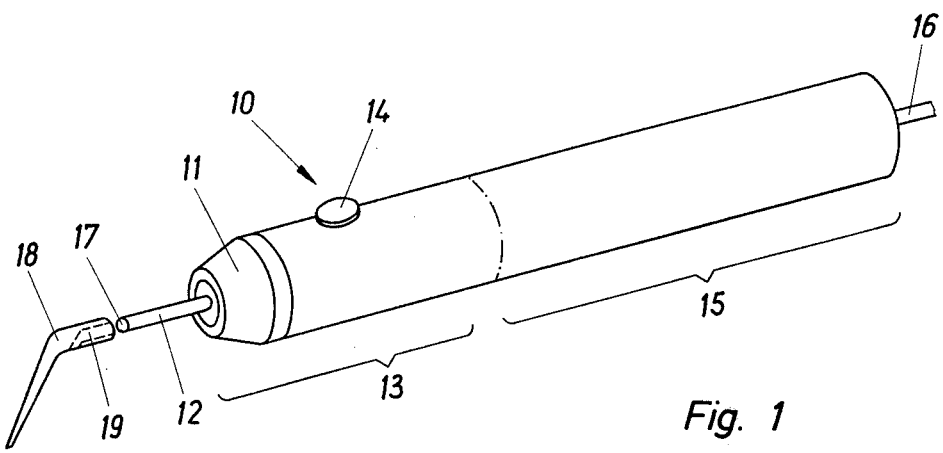
FIG. 1 is a view in perspective of a device related to the invention, especially designed for the removal of tartar from teeth.

FIG. 1 is a slightly enlarged view of a device 10 related to the invention, which is used to generate the ultrasonic vibration, which is particularly designed for the removal of tartar from teeth, but could, to give other examples, be used to atomize liquids such as for use as aerosols or gas propellants, or for manicuring. The device has a head 11, flexibly supported by a copper tube 12, which produces ultrasonic vibrations by means of a piezoelectric vibrator element, which could be an oscillating crystal, located in compartment 13 of the device, when a knob 14 is activated. In a compartment 15 of the device 10, a generator used to excite the crystal is housed, preferably encased in epoxy resin. A hose 16 brings in water used for cooling, which flows through the aperture 17 of the tube 12 into a scraper 18, which can be attached to the end of the tube 12, and into a hole 19 in the latter device, the fluid being atomized as it leaves the hole 19, also serving to wash away the dislodged particles of tartar. An electrical power cable 16' flows parallel to the hose 16 (FIG. 2), supplying the device with a low voltage current, which could be 6 or 12 volts, for example. For special purposes, the device could also be used with battery power, in which case this outside power cable would not be necessary.

Figure 2:
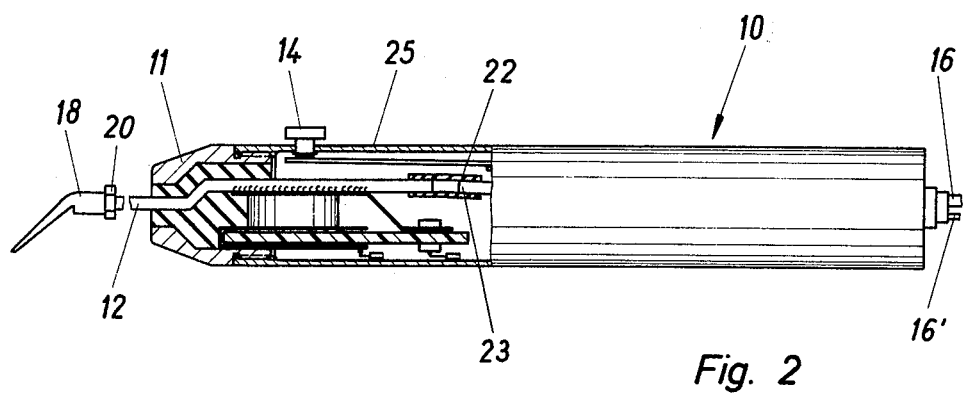
FIG. 2 is a partially sectioned side view of the device of FIG. 1.
Figure 3:
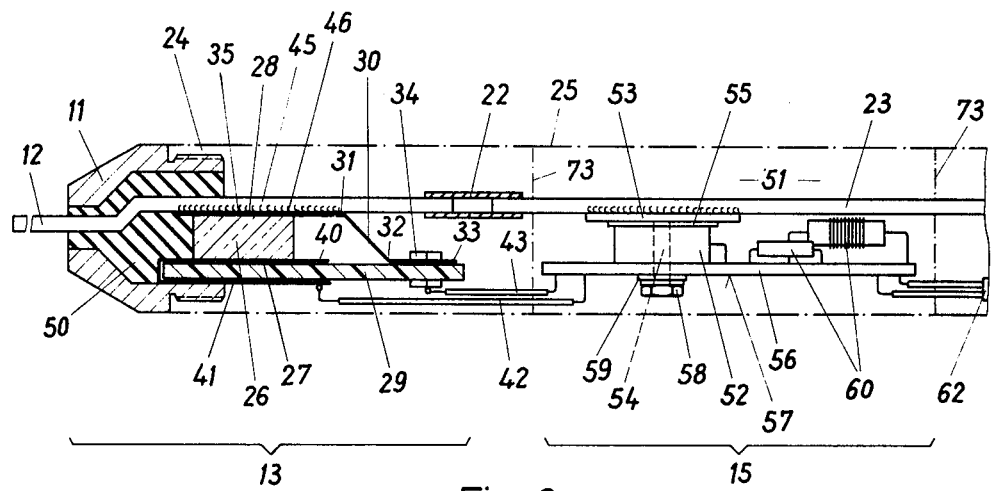
FIG. 3 shows the components located in the interior of the device of FIGS. 1 and 2, the outer casing of the device being indicated by a series of dots and dashes.

FIG. 2 shows a side view of the device 10. The head 11 is shown cut away, in order to show more clearly the shape of the copper tube 12, which forms part of the working tool. The tube 12 is connected, via a piece of flexible tubing 22, to a tube 23, which is in turn connected to the hose 16. A lock nut 20, which is screwed onto the tube 12 along with the scraper 18, makes it possible to mount the tool 18 in a variety of positions. FIG. 3 is an enlarged view of the interior of the device shown in FIGS. 1 and 2. The head 11 is equipped with an exterior thread 24, over which a tube 25, shown only schematically in FIG. 3, may be screwed. This may be made of a metal and used to shield the entire vibrator from the outside, so as to avoid the creation of radio static.

An oscillating crystal 26, which has the appearance of a disk, is suspended by its two flat surfaces 27 and 28, which are silvered by some suitable process, between a carrier 29, which could be a sheet of epoxy resin, and a sring 30, which could be made of phosphor bronze, for example. The spring is bent at two points 31 and 32, so that it has the form of an elongated S. This is riveted by its one free leg 33, by means of a rivet 34, to the carrier 29, while its other free leg 35 lies against the side 28 of the crystal 26, under strong tension. The spring 30 is made in the form of a flat strip, whose width is at least as large as the diameter of the crystal 26. If necessary, the round crystal 26 may be replaced with a crystal of some other profile, such as a right triangle.

Between the side 27 of the crystal 26 and the insulating carrier 29 lies a flat electrical lead 40, bent around the carrier 29 in the shape of a letter U, so that its lower end 41, as shown may be connected to a lead 42, while a lead 43, may be connected to the rivet 34. The crystal 26 is connected with the electric power by means of these leads 42 and 43, which consist of flexible cord, fashioned in some suitable manner.

The copper tube 12, which makes two bends inside the head 11, so that it emerages from the center of the head but, as is shown in FIG. 3, it runs above the center line but parallel to it inside the head of the device 10, is connected by means of this parallel section 45 to the spring 30, in some suitable manner, preferably by a welded or soldered connection 46. Thus it forms a kind of extension of the upper leg 35, of the spring 30 (to the left of it in FIG. 3), i.e., when the left end of the tube 12 (with reference to FIG. 3) is raised or lowered, then the spring 30 turns around the rivet 34 and the section attached to it, which serves as its point of articulation. But if the crystal 26 is excited by the application of an electric current, so that its facets 27 and 28 move back and forth in relation to each other at a given amplitude, then the free end of the tube 12 will transmit vibrations of a magnified amplitude, since the spring 30 and the tube 12 act together in the role of a transmission lever, which magnifies the vibrating amplitude of the crystal 26. This is a matter of special importance, since medical equipment must meet strict specifications with respect to their voltage (6 or 12 volts) and the crystals operate at a very small amplitude of vibration at such low voltages. The vibrating amplitudes of the crystal are thus suitably converted to larger values, making the device shown very suitable for its purpose. There are, of course, a great variety of means for mechanical transmission, many of which are obviously suitable for the same purpose. Such applications would also be within the province of the present invention.

The carrier 29 is fastened in some suitable manner to the head 11, which is suitably provided with a slot to receive this carrier 29, and the carrier 29 may, for example, be cemented into this slot. In order to keep the vibrations of the tube 12 from being transmitted to the head 11, and also in order to make the device 10 airtight and provide support for the tube 12, the head 11 has a filling of silicone rubber 50, in which the crystal 26 and the spring 30 are at least partially encased. Since the carrier 29 is connected to the head 11, and via this to the jacket 25, and thus possesses considerable mass in relationship to that of the crystal 26 and the tube 12, the head 11 and jacket 25 are largely free of vibrations, so that only the tube 12 and the tool 18 attached to it actually vibrate.

As can be further seen from FIG. 3, the section 45 of the tube 12, which runs above the central axis and parallel to it, is connected via the piece of tubing 22, which could be of rubber, to the tube 23, which leads to the generator 51, whose purpose is to excite the crystal 26. A plate 53 is soldered into the tube 23 as a heat trap for a power transistor 52, and onto this plate is fastened a threaded pin 54, which passes through the transistor 52. Between the transistor 52 and the heat trap 53 is a thin mica plate 55, which serves as insulation and as a small capicator inserted between the collector of this transistor and the heat trap 53. On the underside of the transistor 52 (as pictured in FIG. 3) is a plate 56, made of an insulating material, on whose underside is a printed circuit 57. The threaded pin 54 also passes through the plate 56 and a nut 58, which is screwed onto it, under which lies an insulating washer 59, holds together the heat trap 53, the transistor 52, and the plate 56, so that the transistor 52 is in good heat-conducting contact with the heat trap 53. The circuit elements 60, shown here schematically, are soldered in the usual manner to the plate 56, as are also the lead 62 and the lines 42 and 43. The water flowing into the line 23 from the right end (as pictured in FIG. 3) thus cools the heat trap 53 and, indirectly, the transistor 52; it also cools the spring 30 and, as a consequence, the crystal 26, before emerging from the tube 12 in an atomized form. A water-shortage safety valve of a known typé may be inserted into the line 16, to prevent the device 10 from operating without water cooling.

Figure 4:
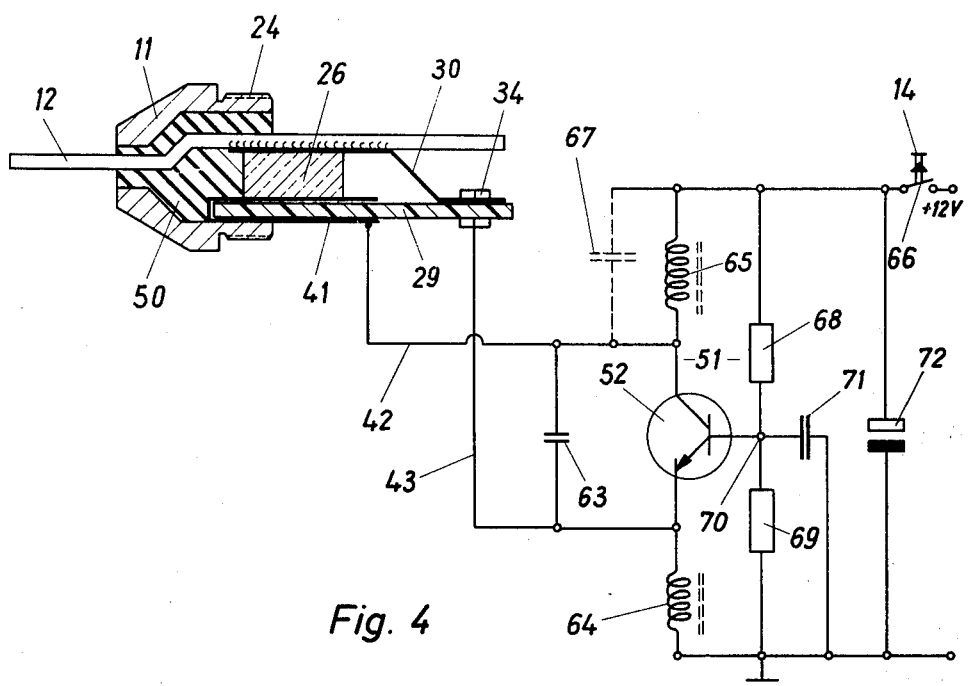
FIG. 4 is a schematic electrical circuit of the device of FIGS. 1-3, connected to the vibrating crystal.

FIG. 4 is a partly schematic diagram of the head 11 with its copper tube 12 and the crystal 26, together with the electrical connections 41 and 34 pertaining to these. The connection 34 is galvanically attached to the tube 12, so that during the treatment of a patient it will be electrically conducting, while the connection 41 is insulated from the patient by the crystal 26.

The generator 51 serves to operate the crystal, this generator being provided with a vibration-resistant npn power transistor 52, to whose collector the line 42 is connected and to whose emitter the line 43 is connected, so that the crystal is connected in parallel with the emitter-collector path of the transistor 52, and therefore to its output side. A small capacitor 63 is also connected in parallel to the crystal 26. The emitter of the transistor 52 is connected to ground via an RF choke 64, so that the tube 12 makes a direct current connection with ground. The collector of the transistor 52 is connected via an RF choke 65 to one terminal of a switch 66, whose other terminal could be connected to +12 volts (if this is the voltage used), the switch being activated by means of the knob 14 (FIGS. 1 and 2). Connected in parallel to the choke 65 is a capacitor 67, which in actual practice consists of a mica plate 55. The choke 65 combines with the capacitor 67 to form a resonant circuit, which is tuned to the frequency of the crystal 26. Between ground and the switch 66 is a voltage divider with two resistors 68 and 69, whose terminal 70 is connected with the base of the transistor 52 and — via a capacitor 71 — with ground. A filter condensor 72 lies between ground and the switch 66. The transistor 52 and its accessory components are made in a suitable manner from epoxy resin, this being indicated by the dot-dash vertical lines 73 in FIG. 3.

Figure 5:
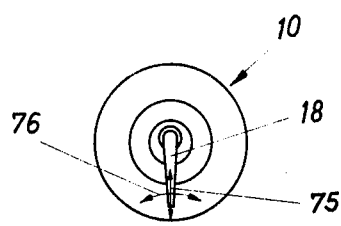
FIG. 5 is a plan view of the device of FIGS. 1-4, as seen from the side of the tool.
Figure 6:
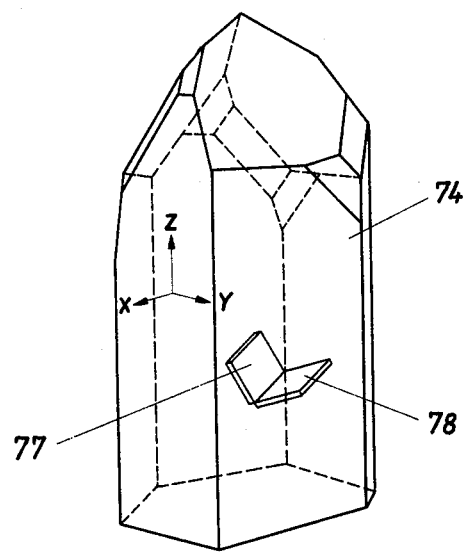
FIG. 6 is a view in perspective of a quartz crystal, showing two ways in which a crystal may be cut in a manner especially suitable for the invention; the usual X-Y-Z system of coordinates is used in the drawing.

The device described above operates as follows:

When the switch 66 is closed by activating the knob 14, the generator, which consists of the crystal 26 and the transistor 52, together with the other elements that form part of the circuit, begins to oscillate at a frequency dependent on the dimensions of the crystal 26, but preferably between 60 and 100 kHz, and more particularly between 100 and 800 kHz. The crystal 26 modifies its mechanical dimensions in rhythm with the electrical oscillations, and these mechanical vibrations are transferred at a magnified amplitude to the tube 12. The point 18 placed over the tube 12 (FIG. 1) creates vibrations in a variety of directions, as is indicated by the arrows in the foreground of FIG. 5. The vibrations 75 are caused by variations in thickness, while the vibrations 76 are the consequence of longitudinal vibrations that move diagonally across the crystal 26. In the form of embodiment shown, a Y-cut crystal is used. FIG. 6 shows a quartz crystal 74 against a system of coordinates, where 77 and 78 are two possibilities for Y-cuts. In the form of embodiment shown, the point 18 thus produces vibrations that are preferably transversal, but longitudinal vibrations may also be created with other forms of embodiment or by some other placement of the crystal. Transversal vibrations are of course preferable for the removal of tartar from teeth, for instance, for the reasons mentioned in the introduction, (where the main purpose is to polish rather than to form grooves).

Devices related to the invention are suitable not only for the removal of tartar but also for other applications, such as for cosmetic treatment or in brain surgery. It has also been demonstrated that fuel can be effectively atomized in a carburator, using this type of vibrator and that considerably improved performance may be achieved in small combustion engines.

What I claim is:

1. A self-contained hand tool for creating and applying ultrasonic vibration for dental use comprising:
   A. handle means comprising a tubular casing of slender elongate form to facilitate holding and manipulation of the hand tool by a user, said casing having a forward end and a rearward end,
   B. a vibrator unit comprising piezoelectric vibrator means mounted in a forward portion of said casing, a vibratable work-tip disposed forwardly of the forward end of said casing and means coupling said work-tip with said piezoelectric vibrator means for transmitting vibration from said vibrator means to said work-tip,
   C. signal generating means disposed in a rearward portion of said casing for generating an alternating electrical signal of ultrasonic frequency, said generating means being spaced from and mechanical vibrationally insulated from said vibrator means in said forward portion of said casing,
   D. circuit means wholly within said casing for electrically connecting said signal generating means with said piezoelectric vibrator means, to apply said ultrasonic alternating electric signal to said piezoelectric vibrator means and thereby excite said vibrator means into ultrasonic oscillation and by such oscillation to produce ultrasonic vibration of said work-tip, said circuit means comprising flexible leads from said generating means to said vibrator means to provide electrical connection but mechanical vibrational insulation between said generating means and said vibrator means,
   E. electrical conductor means electrically connected with said signal generating means and extending from the rearward end of said casing for supplying low voltage direct current to said signal generating means in said casing, and
   F. fluid supply means comprising flexible fluid conduit means extending from the rearward end of said casing to a fluid supply and fluid passage means extending longitudinally through said casing from said fluid conduit means at the rearward end of said casing to the forward end of said casing to deliver fluid to said work-tip, said fluid passage means comprising a rearward portion in heat transmitting relation with said signal generating means to cool the same, a forward portion in heat transmitting relation with said vibrator means to cool the same and an intermediate portion connecting said rearward portion with said forward portion, said intermediate portion of said passage means being flexible to provide mechanical vibrational insulation between said vibrator means and said signal generating means.

2. A hand tool according to claim 1, in which said means coupling said work-tip with said piezoelectric vibrator means comprises means for magnifying the vibration whereby the amplitude of vibration of said work-tip is greater than the amplitude of said vibrator means.

3. A hand tool according to claim 1, in which said means coupling said work-tip with said piezoelectric vibrator means comprises a tubular member which comprises a portion of said passage means.

4. A hand tool according to claim 3, in which said tubular member conducts said fluid to said work-tip, where it is discharged, said fluid being a liquid, whereby vibration of said work-tip and of tubular member produces atomization of said liquid.

5. A hand tool according to claim 1, comprising means for mechanical vibrationally insulating said casing from said piezoelectric vibrator means, work-tip and coupling means.

6. A hand tool according to claim 1, in which said casing comprises a metallic sheath shielding the user from said piezoelectric vibrator means and said signal generating means.

7. A hand tool according to claim 1, in which said work-tip is separate and separable from said coupling means and in which said coupling means comprises means for adjusting the position of and replacing said work-tip.

8. A hand tool according to claim 1, in which said piezoelectric vibrator means comprises means for determining the frequency of said signal generating means, whereby tuning problems are avoided.

9. A hand tool according to claim 1, in which said signal generating means comprises a power transistor electrically connected with said piezoelectric vibrator means and a heat trap in thermal conductive relation with said transistor and with said rearward portion of said fluid passage means, whereby said power transistor is cooled by said fluid.

10. A hand tool according to claim 1, comprising switch means for turning said signal generating means on and off, said switch means including and being controlled by manually operable means on said casing in position for convenient operation by a user holding said hand tool.

11. A hand tool according to claim 10, in which said switch means controls the supply of direct current to said signal generating means.

12. A self-contained hand tool for creating and applying ultrasonic vibration for dental rise comprising,
 A. handle means comprising a tubular casing of slender elongate form to facilitate holding and manipulation of the hand tool by a user, said casing having a forward end and a rearward end,
 B. a vibrator unit comprising piezoelectric vibrator means mounted in a forward portion of said casing, a vibratable work-tip disposed forwardly of the forward end of said casing and means coupling said work-tip to said vibrator means to be vibrated thereby,
 C. signal generating means disposed in a rearward portion of said casing for generating an alternating electrical signal of ultrasonic frequency, said generating means being spaced from and mechanical vibrationally insulated from said vibrator means in said forward portion of said casing,
 D. circuit means wholly within said casing for electrically connecting said signal generating means with said piezoelectric vibrator means, to apply said ultrasonic alternating electrical signal to said piezoelectric vibrator means and thereby excite said vibrator means into ultrasonic oscillation and by such oscillation to produce ultrasonic vibration of said work-tip, said connecting means providing electrical connection but mechanical vibrational insulation between said generating means and said vibrator means,
 E. means including said piezoelectric vibrator means and said electrical connecting means for controlling the frequency of said signal generating means whereby tuning problems are avoided,
 F. electrical conductor means electrically connected with said signal generating means and extending from the rearward end of said casing for supplying low voltage direct current to said signal generating means in said casing, and,
 G. fluid supply means comprising flexible fluid conduit means extending form the rearward end of said casing to a fluid supply and fluid passage means extending longitudinally through said casing from said fluid conduit means at the rearward end of said casing to deliver fluid to said work-tip, said fluid passage means comprising a rearward portion in heat transmitting relation with said signal generating means to cool the same and to warm said fluid, a forward portion in heat transmitting relation with said vibrator means to cool the same and further warm the fluid delivered to said work-tip, and means connecting said rearward portion with said forward portion of said fluid passage means to provide for flow of fluid from said rearward portion to said forward portion of said fluid passage means while providing mechanical vibrational insulation between said vibrator means and said signal generating means.

13. A hand tool according to claim 12, in which said casing comprises a metallic sheath shielding said signal generating means, said piezoelectric vibrator and said circuit means electrically connecting said piezoelectric vibrator means with said signal generating means.

14. A hand tool according to claim 12, in which said signal generating means comprises a power transistor and a resonant circuit tuned to the frequency of said piezoelectric vibrator means.

15. A self-contained hand tool for creating and applying ultrasonic vibration for dental use comprising:
 a. handle means comprising a tubular casing of slender elongate form to facilitate holding and manipulation of the hand tool by a user, said casing having a forward end and a rearward end,
 b. a vibrator unit comprising piezoelectric vibrator means mounted in a forward portion of said casing, a vibratable work-tip disposed forwardly of the forward end of said casing and means coupling said work-tip with said piezoelectric vibrator means for transmitting vibration from said vibrator means to said work-tip,
 c. signal generating means disposed in a rearward portion of said casing for generating an alternating electrical signal of ultrasonic frequency, said generating means being spaced from and mechanical vibrationally insulated from said vibrator means in said forward portion of said casing,
 d. circuit means wholly within said casing for electrically connecting said signal generating means with said piezoelectric vibrator means to apply said ultrasonic alternating electric signal to said piezoelectric vibrator means and thereby excite said vibrator means into ultrasonic oscillation and by such oscillation to produce ultrasonic vibration of said work-tip, said circuit means comprising flexible leads from said generating means to said vibrator means to provide electrical connection but mechanical vibrational insulation between said generating means and said vibrator means,
 e. electrical conductor means electrically connected with said signal generator means and extending from the rearward end of said casing for supplying low voltage direct current to said signal generating means,
 f. switch means for turning said signal generating means on and off, and
 g. fluid supply means comprising flexible fluid conduit means extending from the rearward end of said casing to a fluid supply and fluid passage means extending longitudinally through said casing from said fluid conduit means at the rearward end of said casing to the forward end of said casing to deliver fluid to said work-tip, said fluid passage means comprising a rearward portion in the rearward portion of said casing in heat transmitting relation with said signal generating means to cool the same and to warm the fluid for delivery to said work-tip, a forward portion in the forward portion of said casing containing said vibrator means and an intermediate portion connecting said rearward portion with said forward portion of said fluid passage means, said intermediate portion of said passage means being flexible to provide mechanical vibrational insulation between said vibrator means and said signal generating means.

16. A hand tool according to claim 15, in which said switch means comprises a switch in said casing controlling the supply of direct current to said signal generating means and an operating member on said casing for actuating said switch.

17. A hand tool according to claim 15, in which said casing comprises means electrically shielding said signal generating means and said piezoelectric vibrator means.

* * * * *